United States Patent [19]

Nakamura et al.

[11] Patent Number: 5,155,030

[45] Date of Patent: Oct. 13, 1992

[54] PROCESS FOR PREPARING OPTICALLY ACTIVE (R)-(−)-3-HALO-1,2-PROPANEDIOL FROM AN EPIHALOHYDRIN BY A STRAIN OF CORYNEBACTERIUM OR MICROBACTERIUM

[75] Inventors: Tetsuji Nakamura; Ichiro Watanabe, both of Kanagawa, Japan

[73] Assignee: Nitto Chemical Industry Co., Ltd., Tokyo, Japan

[21] Appl. No.: 511,377

[22] Filed: Apr. 19, 1990

[30] Foreign Application Priority Data

Apr. 21, 1989 [JP] Japan .................................. 1-100174

[51] Int. Cl.$^5$ ............................................. C12P 7/18
[52] U.S. Cl. ..................................... 435/158; 435/157; 435/280; 435/252.1; 435/843
[58] Field of Search ............ 435/157, 158, 280, 252.1, 435/843

[56] References Cited

U.S. PATENT DOCUMENTS 4,840,907 6/1989 Kasai et al. ...................... 435/253.3

Primary Examiner—Douglas W. Robinson
Assistant Examiner—Marian C. Knode
Attorney, Agent, or Firm—Sughrue, Mion, Zinn, Macpeak & Seas

[57] ABSTRACT

A process for preparing an optically active (R)-(−)-3-halo-1,2-propanediol comprising reacting an epihalohydrin with an epihalohydrin hydratase originating from a microorganism. For example, the microorganism belongs to the genus Corynebacterium or the genus Microbacterium. Epihalohydrins which can be used include epichlorohydrin and epibromohydrin. The reaction can be carried out at a temperature of from 5° to 50° C. and a pH of from 4 to 10.

4 Claims, No Drawings

PROCESS FOR PREPARING OPTICALLY ACTIVE (R)-(−)-3-HALO-1,2-PROPANEDIOL FROM AN EPIHALOHYDRIN BY A STRAIN OF CORYNEBACTERIUM OR MICROBACTERIUM

FIELD OF THE INVENTION

This invention relates to a process for preparing an optically active (R)-(−)-3-halo-1,2-propanediol. (R)-(−)-3-halo-1,2-propanediols are known to be useful as starting materials for synthesizing various pharmaceuticals or physiologically active substances, such as L-carnitine, as described in JP-A-57-165352 (corresponding to U.S. Pat. No. 4,413,142) (the term "JP-A" as used herein means an "unexamined published Japanese patent application").

BACKGROUND OF THE INVENTION

Known processes for chemically synthesizing optically active (R)-(−)-3-halo-1,2-propanediols include a process starting with D-mannitol, as disclosed in JP-A-57-165352 (corresponding to U.S. Pat. No. 4,413,142), and a process starting with methyl-5-chloro-5-deoxy-α-L-arabinofuranoside, as disclosed in *Chemistry and Industry*, Jul. 15, 1978, p. 533. These chemical techniques, however, involve complicated procedures and have many problems when carried out on an industrial scale. On the other hand, known biological techniques include a process comprising allowing a microorganism to act on racemic (R,S)-3-halo-1,2-propanediol to selectively metabolize the (S)-(+)-3-halo-1,2-propanediol while retaining the (R)-(−)-3-halo-1,2-propanediol, as disclosed in JP-A-62-158494, and a process comprising allowing a microorganism belonging to the genus Pseudomonas to act on racemic (R,S)-2,3-dichloro-1-propanol to collect (R)-(−)-3-chloro-1,2-propanediol, as disclosed in JP-A-62-69993. However, these biological processes are not economically advantageous because, as a result of the nature of racemate resolution, the molar yield of the desired (R)-(−)-3-halo-1,2-propanediol based on the starting material is only 50% at the highest.

SUMMARY OF THE INVENTION

In view of the above-described situation, the inventors conducted extensive investigations in search of an economical process for industrially producing an optically active (R)-(−)-3-halo-1,2-propanediol. As a result, the inventors found that an optically active (R)-(−)-3-halo-1,2-propanediol can be obtained from an inexpensive racemic epihalohydrin in a molar yield exceeding 50% by the action of an enzyme from a soil microorganism. The present invention is based on this finding.

That is, the present invention relates to a process for preparing an optically active (R)-(−)-3-halo-1,2-propanediol which comprises reacting an epihalohydrin with an epihalohydrin hydratase originating from a microorganism.

Unexpectedly, a desired (R)-(−)-3-halo-1,2-propanediol can be economically obtained in a molar yield exceeding 50% based on the starting material. This occurs even with the use of a racemic compound as a starting material.

DETAILED DESCRIPTION OF THE INVENTION

The epihalohydrin hydratase as used herein means an enzyme capable of producing an (R)-(−)-3-halo-1,2-propanediol from an epihalohydrin. More specifically, such an epihalohydrin hydratase includes an enzyme produced by a microorganism belonging to the genus Corynebacterium (e.g., the strain N-2354) or the genus Microbacterium (e.g., the strain N-4701), both of which were found and isolated from the soil by the inventors. These microorganisms have been deposited with the Fermentation Research Institute, Agency of Industrial Science & Technology, Japan under BIKOKEN-JOKI No. 2726 (FERM BP-2726) (Corynebacterium sp. N-2354) and BIKOKEN-JOKI No. 2644 (FERM BP-2644) (Microbacterium sp. N-4701), respectively. The microbiological properties of these strains are described below.

Strain N-2354;
Morphology: bacillus
Peripheral Cells of Colony: no growth Gram's Stain: +
Existence of Spores: not observed
Mobility: −
Oxidase: +
Catalase: +
O-F Test: oxidative
Growth under Anaerobic Condition: −
Diamino Acid of Cell Wall: diaminobutyric acid
Glycolyl Test: − (acetyl type)
Starch Decomposition: −
Gelatin Liquefaction: −
Hydrogen Sulfide Production:
    Peptone: +
    Sodium Thiosulfate: −
Methyl Red: −
Levan Production: −
Growth in the Presence of NaCl:
    3%: +
    5%: −
Acid Production:
    Inulin: +
    Mannitol: +
    Mannose: +
    Melezitose: −
Strain N-4701
Morphology: polymorphous bacillus
Peripheral Cells of Colony: no growth
Gram's Stain: +
Existence of Spores: not observed
Mobility: +
Flagellum: poles to sides
Color of Colony: yellowish orange
Oxidase: +
Catalase: +
O-F Test: oxidative
Growth under Anaerobic Condition: −
Existence of Mesodiaminopimelic Acid in Hydrolysis Product of Total Cells: −
Diamino Acid of Cell Wall: lysine
Glycolyl Test: +(glycolyl type)
Starch Decomposition: +
Gelatin Liquefaction: −
Nitrate Reduction: −
Utilization of Arginine: +
Hydrogen Sulfide Production: −
Urea Decomposition: −
Temperature Resistance in Skim Milk Medium:
    60° C. ×30 mins
Acid Production:
    Inulin: +

Glycerol: —
Glucose: +
Sucrose: +
Trehalose: +
Raffinose: +

Strains N-2354 and N-4701 were identified as bacteria belonging to the genus Corynebacterium and the genus Microbacterium, respectively, by examining the above-described microbiological properties with reference to *Bergey's Manual of Systematic Bacteriology*, Vol. 2, 1986.

The medium for culturing the above-described microorganisms may have any composition as long as the microorganisms can grow. For example, carbon sources include saccharides (e.g., glucose, fructose, sucrose, maltose), organic acids (e.g., acetic acid, citric acid), and alcohols (e.g., ethanol, glycerol). Nitrogen sources include general naturally occurring nitrogen sources (e.g., peptone, meat extract, yeast extract, protein hydrolysis products, amino acids) and various organic or inorganic ammonium salts. In addition, inorganic salts, traces of metal salts, and vitamins can be used, if necessary. To obtain a high enzyme activity, it is useful to add an epihalohydrin, a 1,3-dihalo-2-propanol, a 3-halo-1,2-propanediol, etc., to the medium.

The microorganism can be cultured in the usual manner (for example, at a pH of from 4 to 10 and at a temperature of from 20° to 40° C. for a period of from 10 to 96 hours under aerobic conditions).

Epihalohydrins which can be used in the present invention as a substrate include epichlorohydrin and epibromohydrin.

The production of an (R)-(−)-3-halo-1,2-propanediol can be carried out by adding the epihalohydrin to a culture medium of the microorganism or a suspension of microbial cells separated from the culture medium by centrifugation, etc.; adding the substrate to a suspension of treated microbial cells (e.g., disrupted microbial cells, microbial cell extracts inclusive of crude enzymes and purified enzymes) or a suspension of microbial cells or treated microbial cells which have been immobilized in a conventional manner; or adding the substrate to culture medium with the microorganism and conducting an enzymatic reaction simultaneously with culturing. Usually, these microbial cells, etc., are suspended in a buffer solution, such as a phosphate or a tris-HCl buffer solution.

The substrate concentration in the reaction system is not particularly limited. Preferably, it ranges from 0.1 to 10 w/v %. The substrate may be added to the reaction system either all at once or in several portions.

The reaction is preferably carried out at a temperature of from 5° to 50° C., more preferably 10° to 35° C., and a pH of from 4 to 10, more preferably 6 to 9.

The reaction time varies depending on the substrate concentration, the cell concentration, and other reaction conditions. Preferably, the reaction conditions should be set so that the reaction can be completed within 1 to 120 hours.

The (R)-(−)-3-halo-1,2-propanediol thus produced and accumulated in the reaction mixture can be recovered and purified through known techniques. For example, the microbial cells can be separated from the reaction mixture by centrifugation and the like and extracted with ethyl acetate, etc., and the extracting solvent can be removed under reduced pressure to recover the desired (R)-(−)-3-halo-1,2-propanediol as a syrup. If desired, the syrup can be further purified by distillation under reduced pressure.

The present invention will now be illustrated in greater detail by way of the following Examples, but it should be understood that the present invention is not construed as being limited thereto. Unless otherwise indicated, all parts, percents, and ratios are by weight.

EXAMPLE 1

A medium containing 1% glucose, 0.5% peptone, 0.3% meat extract and 0.3% yeast extract was adjusted to a pH of 7.0, and 100 ml of the medium was charged into a 500 ml-volume Erlenmeyer flask. After sterilization at 120° C. for 15 minutes, 0.8 ml of a 25 w/v % aqueous solution of 3-chloro-1,2-propanediol having been filtered through a membrane filter was added thereto.

The strain N-4701 (BIKOKEN-JOKI No. 2644, FERM BP-2644) was inoculated into the medium and shake-cultured at 30° C. for 48 hours. Microbial cells were collected from the culture by centrifugational separation, suspended in a 20 mM phosphate buffer solution (pH 7.0) containing 5 mM mercaptoethanol, and disrupted by French Press at 1,500 kg/cm$^2$. After dialysis, the cell suspension was subjected to column chromatography using DEAE-Sephacell to obtain a partially purified enzyme solution. 10 ml of the enzyme solution was added to 40 ml of a 1M tris-HCl buffer solution (pH 8.0), and 0.5 g of epichlorohydrin was added thereto, followed by stirring at 20° C. to conduct the reaction. Two hours later, gas chromatography indicated that 3-chloro-1,2-propanediol had been produced at a molar yield of 93.5% based on the charged epichlorohhdrin.

The reaction mixture was extracted three times with 50 ml portions of ethyl acetate, and the extract was dehydrated over anhydrous sodium sulfate. The solvent was removed under reduced pressure to obtain a syrup of 3-chloro-1,2-propanediol.

The 3-chloro-1,2-propanediol was tosylated by the reaction with p-toluenesulionic acid, and subjected to high performance liquid chromatography (HPLC) using a "Chiralcell OC" column produced by Daisel Ltd. to analyze optical isomers. The R/S molar ratio was found to be 61.3:38.7, which means that the molar yield of (R)-(−)-3-chloro-1,2-propanediol based on the charged epichlorohydrin was 57.3%.

EXAMPLE 2

The strain N-2354 (BIKOKEN-JOKI No. 2726, FERM BP-2726) was inoculated into the same medium as was prepared in Example 1 and shake-cultured at 30° C. for 48 hours. Microbial cells collected from 140 ml of the culture by centrifugation were washed with 140 ml of a 100 mM tris-HCl buffer solution (pH 8.0) and suspended in 35 ml of a 1 M tris-HCl buffer solution (pH 8.0). 0.35 g of epichlorohydrin was added to the suspension, and the system was stirred at 20° C. for 3.5 hours to conduct the reaction. After completion of the reaction, gas chromatography indicated that 3-chloro-1,2-propanediol had been produced at a molar yield of 78.8% based on the charged epichlorohydrin.

The reaction mixture was extracted three times with 50 ml portions of ethyl acetate, and the extract was dehydrated over anhydrous sodium sulfate. The solvent was removed under reduced pressure to obtain a syrup of 3-chloro-1,2-propanediol. The 3-chloro-1,2-propanediol was tosylated by the reaction with p-toluenesulfonic acid, and analyzed by HPLC using a "Chiralcell OC" column. As a result, the R/S molar ratio was found to be 66.0:34.0, which means that the molar yield of (R)-(−)-3-chloro-1,2-propanediol based on the charged epichlorohydrin was 52.0%.

While the invention has been described in detail and with reference to specific embodiments thereof, it will be apparent to one skilled in the art that various changes and modifications can be made therein without departing from the spirit and scope thereof.

What is claimed is:

1. A process for the production of an optically active (R)-(−)-3-halo-1,2-propanediol comprising incubating epichlorohydrin or epibromohydrin with Corynebacterium N-2354, Nicrobacterium N-4701, or an extract thereof under conditions effective for the production of (R)-(−)-3-halo-1,2-propanediol and recovering the (R)-(−)-3-halo-1,2-propanediol.

2. A process as claimed in claim 1, further comprising adding at least one of an epihalohydrin, a 1,3-dihalo-2-propanol, and a 3-halo-1,2-propanediol to enhance enzymatic activity.

3. A process as claimed in claim 1, wherein said epihalohydrin is present as a substrate at a concentration of from 0.1 to 10 w/v %.

4. A process as claimed in claim 1, wherein said reaction is carried out at a temperature of from 5° to 50° C. and a pH of from 4 to 10.

* * * * *